(12) United States Patent
Mehta et al.

(10) Patent No.: US 7,465,751 B2
(45) Date of Patent: Dec. 16, 2008

(54) 1-SUBSTITUTED-3-PYRROLIDINE DERIVATIVES AS MUSCARINIC RECEPTOR ANTAGONISTS

(75) Inventors: Anita Mehta, Plainfield, IL (US); Jang Bahadur Gupta, Dusseldorf (DE); Pakala Kumara Savithru Sarma, Haryana (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 0 days.

(21) Appl. No.: 10/540,245

(22) PCT Filed: Dec. 23, 2002

(86) PCT No.: PCT/IB02/05590

§ 371 (c)(1),
(2), (4) Date: Feb. 7, 2006

(87) PCT Pub. No.: WO2004/056767

PCT Pub. Date: Jul. 8, 2004

(65) Prior Publication Data

US 2006/0194862 A1 Aug. 31, 2006

(51) Int. Cl.
*A61K 31/4015* (2006.01)
*A61K 31/4025* (2006.01)
*C07D 207/48* (2006.01)
*C07D 207/12* (2006.01)

(52) U.S. Cl. .................. 514/422; 514/424; 548/541; 548/542; 548/525; 548/526

(58) Field of Classification Search ............... 548/519, 548/529, 518, 541, 542, 525, 526; 514/422, 514/424
See application file for complete search history.

(56) References Cited

U.S. PATENT DOCUMENTS

| | | | | |
|---|---|---|---|---|
| 2,956,062 | A | 10/1960 | Lunsford | 260/326.3 |
| 3,091,570 | A | 5/1963 | Biel | 167/65 |
| 3,176,019 | A | 3/1965 | Campbell et al. | 260/293.4 |
| 5,281,601 | A | 1/1994 | Cross et al. | 514/320 |
| 5,948,792 | A | 9/1999 | Tsuchiya et al. | 514/317 |
| 6,130,232 | A | 10/2000 | Mase et al. | 514/318 |
| 6,174,900 | B1 | 1/2001 | Okada et al. | 514/317 |

FOREIGN PATENT DOCUMENTS

| | | |
|---|---|---|
| EP | 0 012 071 | 6/1980 |
| EP | 0 325 571 | 7/1989 |
| EP | 0 388 054 | 9/1990 |
| EP | 0 801 067 | 10/1997 |
| EP | 0 823 423 | 2/1998 |
| EP | 0 863 141 | 9/1998 |
| EP | 0 930 298 | 7/1999 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16048 | 8/1993 |
| WO | WO 96/33973 | 10/1996 |
| WO | WO 97/45414 | 12/1997 |
| WO | WO 98/00016 | 1/1998 |
| WO | WO 98/00109 | 1/1998 |
| WO | WO 98/00132 | 1/1998 |
| WO | WO 98/00133 | 1/1998 |
| WO | WO 98/05641 | 2/1998 |
| WO | WO 98/21183 | 5/1998 |
| WO | WO 98/29402 | 7/1998 |
| WO | WO 02/04402 | 1/2002 |

OTHER PUBLICATIONS

Bundgaard, Design of prodrugs, 1985, Elsevier, p. 1-9.*
Maureen Rouhi, Chemical & Engineering News, Feb. 24, 2004, p. 32-35.*
Haleblian et al. Journal of Pharmaceutical Science, Aug. 1969, vol. 58, No. 8, p. 911-912.*
Koppanyi, 88:130844, 1974.*
Kubo et al., "Cloning, sequencing and expression of complementary DNA encoding the muscarinic acetylcholine receptor", *Nature*, 323(2):411-416 (1986).
Bonner et al., "Identification of a Family of Muscarinic Acetylcholine Receptor Genes", *Science*, 237:527-531 (1987).
Eglen et al., "Muscarinic Receptor Ligands and Their Theraputic Potential", *Current Opinions in Chemical Biology*, 3(4):426-432 (1999) XP000972296, ISSN: 1367-5931.
Eglen et al., "Theraputic opportunities from muscarinic receptor research", *Trends in Pharmacological Sciences*, 22(8):409-414 (2001).

(Continued)

*Primary Examiner*—Joseph McKane
*Assistant Examiner*—Jason M Nolan
(74) *Attorney, Agent, or Firm*—Jayadeep R. Deshmukh, Esq.; George E. Heibel, Esq.

(57) ABSTRACT

This invention generally relates to the derivatives of 1-substituted-3-pyrroli dines having the structure of Formula (I): The compounds of this invention can function as muscarinic receptor antagonists, and can be used for the treatment of various diseases of the respiratory, urinary and gastrointestinal systems mediated through muscarinic receptors. The invention also relates to a process for the preparation of the compounds of the present invention. pharmaceutical compositions containing the compounds of the present invention and the methods for treating the diseases mediated through muscarinic receptors.

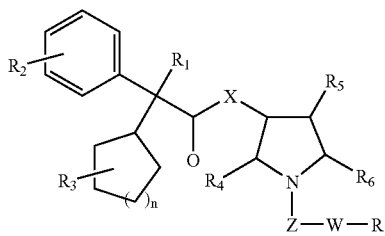

2 Claims, No Drawings

OTHER PUBLICATIONS

Felder et al., "Theraputic Opportunities for Muscarinic Receptors in the Central Nervous System", *Journal of Medicinal Chemistry*, 43(23):4333-4353 (2000).

Broadley and Kelly, "Muscarinic Receptor Agonists and Antagonists", *Molecules*, 6:142-193 (2001).

Birdsall et al., "Muscarinic receptors: it's a knockout", *Trends in Pharmacological Sciences*, 22(5):215-219 (2001).

de Groat and Yoshimura, "Pharmacology of the Lower Urinary Tract", *Annual Review of Pharmacology and Toxicology*, 41:691-721 (2001).

Steers, "The future direction of neuro-urology drug research", *Current Opinion in CPNS Investigational Drugs*, 2(3):268-282, (2000).

Chapple, "Muscarinic receptor antagonists in the treatment of overactive bladder", *Urology*, 55(Suppl. 5A):33-46 (2000).

Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).

Sagara et al., "Cyclohexylmethylpiperidinyltriphenylpropioamide: A Selective Muscarinic $M_3$ Antagonist Discriminating against the Other Receptor Subtypes", *Journal of Medicinal Chemistry*, 45:984-987 (2002) XP002238502, ISSN: 0022-2623.

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Cheng and Prusoff, "Relationship between the inhibition constant $(K_1)$ and the concentration of inhibitor which causes 50 per cent inhibition $(I_{50})$ of an enzymatic reaction", *Biochemical Pharmacology*, 22:3099-3108 (1973).

Franko et al., "Derivatives of 3-Pyrrolidinols-III. The Chemistry, Pharmacology, and Toxicology of some N-Substituted-3-Pyrrolidyl alpha-Substituted Phenylacetates", *Journal of Medicinal and Pharmaceutical Chemistry*, 2:523-540 (1960).

Biel et al., "Central Stimulants. II. Cholinergic Blocking Agents", *Journal of Organic Chemistry, American Chemical Society*, 26, 4096-4103 (1961).

Taniguchi et al., "Agents for the Treatment of Overactive Detrusor. VI. Synthesis and Pharmacological Properties of Acetamide Derivatives Bearing Cyclic Amines in N-Substituents", *Chemical and Pharmaceutical Bulletin*, 42(1):74-84 (1994).

O'Neill et al., "Biochemical effects of psychotomimetic anticholinergic drugs", *Advances in Biochemical Psychopharmacology*, 6:203-218 (1972).

\* cited by examiner

1-SUBSTITUTED-3-PYRROLIDINE DERIVATIVES AS MUSCARINIC RECEPTOR ANTAGONISTS

FIELD OF THE INVENTION

This invention generally relates to the derivatives of 1-substituted-3-pyrrolidines.

The compounds of this invention can function as muscarinic receptor antagonists, and can be used for the treatment of various diseases of the respiratory, urinary and gastrointestinal systems mediated through muscarinic receptors.

The invention also relates to a process for the preparation of the compounds of the present invention pharmaceutical compositions containing the compounds of the present invention and the methods for treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527).

A review in *Current Opinions in Chemical Biology* 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in *J. Med. Chem.*, 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 2001, 6: 142.

N. J. M. Birdsall et. al. in *Trends in Pharmacological Sciences* 2001; 22: 215 have also summarized the recent developments on the role of different muscarinic receptor subtypes using different muscaranic receptors of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarternary derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of *Pharmacological Toxicol.*, 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in *Curr. Opin. Invest. Drugs*, 2: 268, C. R. Chapple et. al. in *Urology* 55: 33), Steers W D, Barrot D M, Wein A J, 1996, Voiding dysfunction: diagnosis classification and management. In "Adult and Pediatric Urology," ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other close art references.

A report in *J. Med. Chem.*, 2002; 44:984, describes cyclohexylmethyl piperidinyl triphenylpropioamide derivatives as selective $M_3$ antagonist discriminating against the other receptor subtypes.

PCT applications WO 98/00109; 98/00132; 98/00133 and 98/00016 disclose isomers of glycopyrolate.

SUMMARY OF THE INVENTION

The present invention provides 1-substituted-3-pyrrolidines which function as muscarinic receptor antagonists and are useful as safe and effective therapeutic or prophylactic agents for the treatment of various diseases of the respiratory, urinary and gastrointestinal systems and process for the synthesis of the compounds.

The invention also provides pharmaceutical compositions containing the compounds, and which may also contain acceptable carriers, excipients or diluents which are useful for the treatment of various diseases of the respiratory, urinary and gastrointestinal systems.

The invention also includes the enantiomers, diastereomers, polymorphs, pharmaceutically acceptable salts, pharmaceutically acceptable solvates, esters, N-oxides and metabolites of these compounds having the same type of activity.

The invention further includes pharmaceutical compositions comprising the compounds of the present invention, their esters, metabolites, enantiomers, diastereomers, N-oxides, polymorphs, pharmaceutically acceptable salts or pharmaceutically acceptable solvates, in combination with a pharmaceutically acceptable carrier and optionally included excipients.

Other advantages of the invention will be set forth in the description which follows, and in part will be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

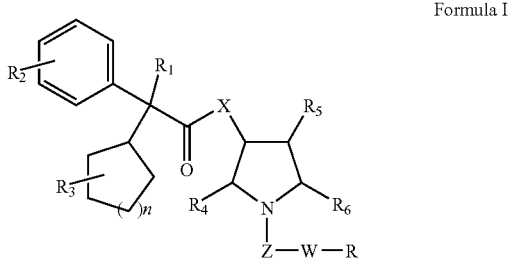

Formula I and its pharmaceutically acceptable salts, pharmaceutically acceptable solvates, esters, enantiomers, diastereomers, N-oxides, polymorphs, prodrugs, or metabolites, wherein X represents an oxo, amino, lower alkyl($C_1$-$C_4$)amino or lower alkoxy ($C_1$-$C_4$);

$R_1$ represents hydroxy, amino, or alkoxy ($OR_7$), wherein $R_7$ represents lower alkyl;

$R_2$ represents hydrogen, halogen (e.g. fluorine, chlorine, bromine and iodine) or lower alkyl;

$R_3$ represents hydrogen, keto, hydroxy, sulphonyl methane, tosyl, azide, amino or substituted amine ($N_8$) where $R_8$ represents hydrogen or $YR_9$, wherein $R_9$ represents benzyl, benzyloxy, alkyl, benzyl ether, phenyl optionally substituted with alkyl, trifluoromethyl, nitro or halogen (e.g. fluorine, chlorine, bromine, iodine);

Z represents methylene, sulphonyl or carbonyl;

W represents a direct link of $(CH_2)_n$, where n is 1 or 2, lower alkoxy ($C_1$-$C_4$) or lower thioalkoxy ($C_1$-$C_4$);

R represents alkyl, aryl, aralkyl, benzyl ether, dimethyl ether, methoxy methyl, benzyl methyl ether or phenyl optionally substituted with alkyl, halogen (e.g. fluorine, chlorine, bromine, iodine), nitro, heterocycle selected from the group consisting of pyridinyl, pyrazinyl or thienyl;

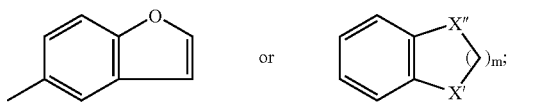

wherein X' and X" are each independently selected from the group consisting of oxygen, methylene; m represents 1 to 3; and $R_4$, $R_5$ and $R_6$ represent hydrogen or lower alkyl.

In accordance with a second aspect of the present invention, there is provided a method for treatment or prophylaxis of an animal or human suffering from a disease or disorder of the respiratory, urinary and gastrointestinal systems, wherein the disease or disorder is mediated through muscarinic receptors, comprising administering to a patient in need thereof, an effective amount of compounds as described above.

In accordance with a third aspect of the present invention, there is provided a method for treatment or prophylaxis of an animal or human suffering from a disease or disorder associated with muscarinic receptors, comprising administering to a patient in need thereof, an effective amount of compounds as described above.

In accordance with a fourth aspect of the present invention, there is provided a method for treatment or prophylaxis of an animal or human suffering from a disease or disorder of the urinary system which induce such urinary disorders as urinary incontinence, lower urinary tract symptoms (LUTS), etc.; respiratory system such as bronchial asthma, chronic obstructive pulmonary disorders (COPD), pulmonary fibrosis, etc; and gastrointestinal system such as irritable bowel syndrome, obesity, diabetes and gastrointestinal hyperkinesis with compounds as described above, wherein the disease or disorder is associated with muscarinic receptors.

In accordance with a fifth aspect of the present invention, there is provided a process for preparing the compounds as described above.

The compounds of the present invention exhibit significant potency in terms of their activity, which was determined by in vitro receptor binding and functional assays and in vivo experiments using anaesthetized rabbit. Compounds were tested in vitro and in vivo. Some compounds were found to function as potent muscarinic receptor antagonists with high affinity towards $M_3$ receptors. Therefore, the present invention provides pharmaceutical compositions for treatment of the diseases or disorders associated with muscarinic receptors. Compounds and compositions described herein can be administered orally or parenterally.

DETAILED DESCRIPTION OF THE INVENTION

The compounds described herein may be prepared by techniques well known in the art and familiar to the average synthetic organic chemist. In addition, the compounds described herein may be prepared by the following reaction sequence:

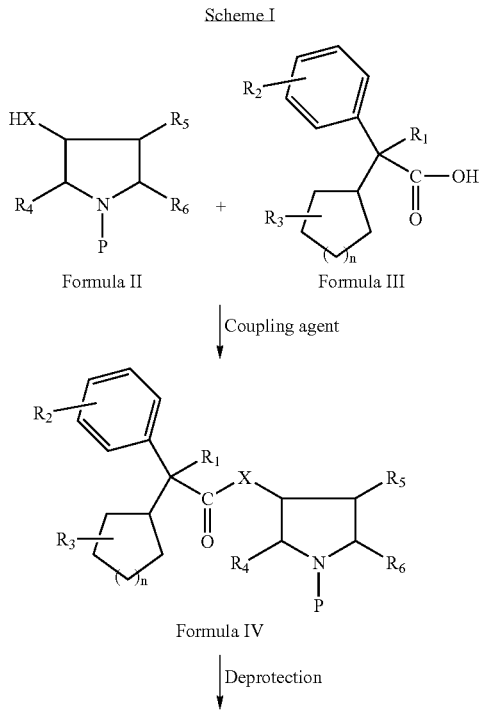

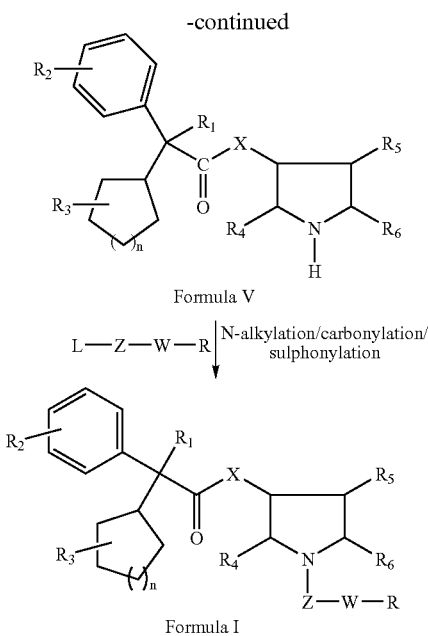

Formula V

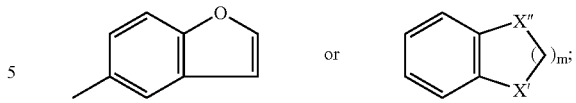

wherein X' and X" are each independently selected from the group consisting of oxygen, methylene; and m represents 1 to 3.

The reaction of the compound of Formula II with a compound of Formula III to give a compound of Formula IV can be carried out in the presence of a coupling agent, for example, N-methyl morpholine, hydroxy benzotriazole,1-(3-dimethylaminopropyl)-3-ethyl carbodiimide hydrochloride (EDC. HCL) and 1,8-diazabicyclo[5.4.0]undec-7-ene (DBU).

The reaction of the compound of Formula II with a compound of Formula III to give a compound of Formula IV can be carried out in a suitable solvent, for example, N,N-dimethylformamide, chloroform, dimethylsulphoxide, xylene and toluene.

The deprotection of the compound of Formula IV to give a compound of Formula V can be carried out in the presence of a deprotecting agent, for example, palladium on carbon, ammonium formate, trifluoroacetic acid and hydrochloric acid.

The deprotection of the compound of Formula IV to give a compound of Formula V can be carried out in a suitable solvent, for example, methanol, ethanol, tetrahydrofuran and acetonitrile at temperatures ranging from about 10 to about 50° C.

The N-alkylation, carbonylation or sulphonylation of the compound of Formula V to give a compound of Formula I can be carried out with a suitable alkylating, carbonylating, or sulphonylating agent, L-Z-W-R where L is any leaving group known in the art, for example halogen, O-mestyl, benzyl and O-tosyl group.

The N-alkylation or carbonylation or sulphonylation of the compound of Formula V to give a compound of Formula I can be carried out in a suitable solvent such as N,N-dimethylformamide, dimethylsulfoxide, tetrahydrofuran, acetonitrile and dichloromethane.

In the above scheme, where specific bases, coupling agents, protecting groups, deprotecting agents, N-alkylating, sulphonylating, cabonylating agents, solvents, catalysts etc. are mentioned, it is to be understood that other bases, coupling agents deprotecting agents, N-alkylating, sulphonylating, carbonylating agents, solvents etc. known to those skilled in art may be used. Similarly, the reaction temperature and duration may be adjusted according to the desired needs.

The pharmaceutically acceptable salts of the compounds of Formula I include acid addition salts such as hydrochloride, hydrobromide, hydrofluoric, sulphate, bisulfate, phosphate, hydrogen phosphate, acetate, brosylate, citrate, fumarate, glyconate, lactate, maleate, mesylate, succinate, and tartarate.

Quaternary ammonium salts such as alkyl salts, aralkyl salts, and the like, of the organic bases may be readily formed by treatment of the organic bases with the appropriate quaternary salts forming substances, which include, for example methyl chloride, methyl bromide, methyl iodide, methyl sulphate, methyl benzene sulphonate, methyl p-toluene sulphonate, ethyl chloride, ethyl bromide, ethyl iodide, n-propyl chloride, n-propyl bromide, n-propyl iodide, isopropyl bromide, n-butyl chloride, n-butyl bromide, isobutyl bromide, Formula I The compounds of Formula I of the present invention may be prepared by the reaction sequence as shown in scheme I. The preparation comprises coupling a compound of Formula II with the compound of Formula III wherein X represents an oxo, amino, lower alkyl($C_1$-$C_4$)amino or lower alkoxy ($C_1$-$C_4$);

$R_1$ represents hydroxy, amino, or alkoxy ($OR_7$), wherein $R_7$ represents lower alkyl;

$R_2$ represents hydrogen, halogen (e.g. fluorine, chlorine, bromine and iodine) or lower alkyl;

$R_3$ represents hydrogen, keto, hydroxy, sulphonyl methane, tosyl, azide, amino or substituted amine ($NHR_8$) where $R_8$ represents hydrogen or $YR_9$, wherein $R_9$ represents benzyl, benzyloxy, alkyl, benzyl ether, phenyl optionally substituted with alkyl, trifluoromethyl, nitro or halogen (e.g. fluorine, chlorine, bromine, iodine);

$R_4$, $R_5$ and $R_6$ represent hydrogen or lower alkyl;

N is 1 or 2; and

P is any group, for example benzyl, t-buyloxycarbonyl, which can be used to protect an amino group in the presence of a coupling agent to give a protected compound of Formula IV, which on deprotection through reaction with a deprotecting agent in an organic solvent gives an unprotected compound of Formula V which is finally N-alkylated, carbonylated or sulphonylated with a suitable alkylating, carbonylating or sulphonylating agent of Formula L-Z-W-R to give a compound of Formula I, wherein L is a leaving group and Z represents methylene, sulphonyl or carbonyl;

W represents a direct link of $(CH_2)_n$, where n is 1 or 2, lower alkoxy ($C_1$-$C_4$) or lower thioalkoxy ($C_1$-$C_4$); and R represents alkyl, aryl, aralkyl, benzyl ether, dimethyl ether, methoxy methyl, benzyl methyl ether or phenyl optionally substituted with alkyl, halogen (e.g. fluorine, chlorine, bromine, iodine), nitro, heterocycle selected from the group consisting of pyridinyl, pyrazinyl or thienyl;

sec-butylbromide, n-amyl bromide, n-hexyl chloride, benzyl chloride, benzyl bromide, and ethyl sulphate.

Particular compounds which are capable of being produced by Scheme I and shown in Table I include:

Compound No. Chemical Name
1. 2-cyclopentyl-2-hydroxy-N-[(3S)-1-benzyl-pyrrolidin-3-yl]-2-phenyl acetamide
2. 2-cyclopentyl-2-hydroxy-N-[(3S)-1-[2-(1,3-benzodioxol-5-yl)]-ethyl]pyrrolidin-3-yl]-2-phenyl acetamide
3. (3S)-1-benzylpyrrolidin-3-yl cyclopentyl(hydroxy)phenyl acetate
4. (3S)-1-[[2-(,3-benzodioxol-yl)ethyl]pyrrolidin-3yl]cyclopentyl(hydroxy)phenyl acetate
5. (3S)-1-[[2-(2,3-dihydro-1-benzofuran-5-yl)ethyl]pyrrolidin-3-yl]cyclopentyl-(hydroxy)phenyl acetate
6. (3S)-1-[(4-methyl-pent-3-enyl)pyrrolidin-3-yl]cyclopentyl(hydroxy)phenyl acetate
7. (3S)-1-[(4-trifluoromethylphenyl)sulfonyl]pyrrolidin-3-yl]cyclopentyl(hydroxy) phenyl acetate
8. (3S)-1-[(4-nitrophenyl]sulfonyl]pyrrolidin-3-yl]cyclopentyl(hydroxy)phenyl acetate
9. (3S)-1-benzyl-pyrrolidin-3-yl (2R)-hydroxy(3-oxocyclopentyl)phenyl acetate
10. (3S)-1-benzylpyrrolidin-3-yl (2R)-hydroxy(3-hydroxycyclopentyl)phenyl acetate
11. (3S)-1-[(phenylacetyl)pyrrolidin-3-yl]cyclopentyl(hydroxy)phenyl acetate
12. (3S)-1-[(benzyloxy)acetyl]pyrrolidin-3-yl]cyclopentyl (hydroxy)phenyl acetate
13. Benzyl (3S)-3-[(2-hydroxy-2-cyclopentyl-2-phenylpropanoyl)oxy]pyrrolidin-1-carboxylate
14. (3S)-1-[(4-bromophenyl)sulfonyl]pyrrolidin-3-yl]cyclopentyl(hydroxy)phenyl acetate
15. (3S)-1-benzylpyrrolidin-3-yl (2R)-cyclopentyl(hydroxy) phenyl acetate
16. (3S)-1-[[2-(2,3-dihydro-1-benzofuran-5-yl)ethyl]pyrrolidin-3-yl] (2R)cyclopentyl(hydroxy)phenyl acetate
17. (3S)-1-[[2-(1,3-benzodioxol-5-yl)ethyl]pyrrolidin-3-yl (2R)-cyclopentyl(hydroxy) phenyl acetate

TABLE I

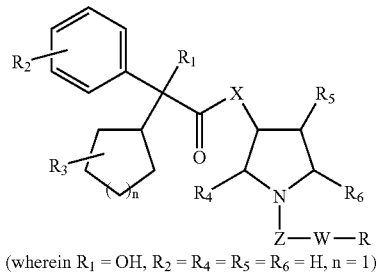

Formula I (wherein $R_1$ = OH, $R_2$ = $R_4$ = $R_5$ = $R_6$ = H, n = 1)

| Compound No. | Z—W—R | X | $R_3$ | Configuration at pyrrolidine | Configuration at Carbon attached to $R_1$ |
|---|---|---|---|---|---|
| 1. | (benzyl) | NH | H | S | RS |
| 2 | (benzodioxole-ethyl) | NH | H | S | RS |
| 3. | (benzyl) | O | H | S | RS |
| 4. | (benzodioxole-ethyl) | O | H | S | RS |
| 5. | (dihydrobenzofuran-ethyl) | O | H | S | RS |
| 6. | (4-methyl-pent-3-enyl) | O | H | S | RS |

TABLE I-continued
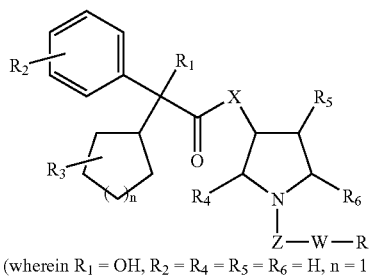
Formula I
(wherein R₁ = OH, R₂ = R₄ = R₅ = R₆ = H, n = 1)
| Compound No. | Z—W—R | X | R₃ | Configuration at pyrrolidine | Configuration at Carbon attached to R₁ |
|---|---|---|---|---|---|
| 7. | 4-CF₃-C₆H₄-SO₂ | O | H | S | RS |
| 8. | 4-NO₂-C₆H₄-SO₂ | O | H | S | RS |
| 9. | C₆H₅-CH₂ | O | CO | S | RS |
| 10. | C₆H₅-CH₂ | O | OH | S | RS |
| 11. | COCH₂-C₆H₅ | O | H | S | RS |
| 12. | COCH₂OCH₂-C₆H₅ | O | H | S | RS |
| 13. | COOCH₂-C₆H₅ | O | H | S | RS |
| 14. | 4-Br-C₆H₄-SO₂ | O | H | S | RS |
| 15. | C₆H₅-CH₂ | O | H | S | R |
| 16. | 2,3-dihydrobenzofuran-5-yl-CH₂ | O | H | S | R |

TABLE I-continued

Formula I (wherein $R_1$ = OH, $R_2$ = $R_4$ = $R_5$ = $R_6$ = H, n = 1)

| Compound No. | Z—W—R | X | $R_3$ | Configuration at pyrrolidine | Configuration at Carbon attached to $R_1$ |
|---|---|---|---|---|---|
| 17. | (benzodioxole-CH₂-) | O | H | S | R |

Compounds or compositions disclosed may be administered to an animal for treatment orally, or by a parenteral route. Pharmaceutical compositions disclosed herein can be produced and administered in dosage units, each unit containing a certain amount of at least one compound described herein and/or at least one physiologically acceptable addition salt thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes the enantiomers, diastereomers, N-oxides, polymorphs, solvates and pharmaceutically acceptable salts of these compounds as well as metabolites having the same type of activity. The present invention further includes pharmaceutical composition comprising the compounds of Formula I, their esters, metabolites, enantiomers, diastereomers, N-oxides, polymorphs, solvates or pharmaceutically acceptable salts thereof, in combination with pharmaceutically acceptable carrier and optionally included excipients.

The examples mentioned below demonstrate the general synthetic procedure as well as the specific preparation of the preferred compounds. The examples are provided to illustrate particular aspects of the disclosure and should not be construed to limit the scope of the present invention as defined by the claims.

EXPERIMENTAL DETAILS

Various solvents, such as acetone, methanol, pyridine, ether, tetrahydrofuran, hexane and dichloromethane were dried using various drying reagents according to the procedures well known in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

EXAMPLE 1

Preparation of 2-cyclopentyl-2-hydroxy-N-[(3S)-1-benzyl-pyrrolidin-3-yl]-2-phenylacetamide (Compound No. 1)

Step 1: Preparation of (3R)-pyrrolidin-3-ol hydrochloride

The compound trans-4-hydroxy-L-proline (10.0 g, 76.3 mM) was taken in a mixture of anhydrous cyclohexanol (50.0 ml) and 2-cyclohexen-1-one (0.5 ml). The reaction mixture was heated at 155-160° C. for about 11 hours. To the reaction mixture, ethanolic hydrochloric acid (70.0 ml) was added with constant stirring, and kept at 0-5° C. overnight. The separated solid was filtered under nitrogen atmosphere, washed with ethyl acetate (10.0 ml) and dried under vacuum to get the title compound. Yield=35% (3.3 g, 26.7 mM).

$^1$H NMR (DMSO-$d_6$): δ 9.57 (brs, 1H), 9.33 (brs, 1H), 5.00-5.75 (brs, 1H), 4.38 (s, 1H), 3.01-3.47 (m, 4H), 1.84-1.92 (m, 2H).

Step 2: Preparation of (3R)-1-benzyl-pyrrolidin-3-ol

The compound (3R)-pyrrolidin-3-ol hydrochloride (2.2 g, 17.8 mM) was dissolved in dichloromethane (25.0 ml) and triethylamine (5.0 ml, 35.6 mM) was added at room temperature with constant stirring for 5 minutes. Benzyl chloride (2.5 ml, 21.4 mM) was added to it in one lot at the same temperature followed by refluxing for 15 hours. The reaction mixture was diluted with chloroform and 1N sodium hydroxide (15.0 ml) was added with constant stirring for 10 minutes. The organic layer was separated and washed with aqueous sodium bicarbonate and brine solution. It was further dried over anhydrous sodium sulphate and concentrated to get the title compound. Yield=44.4% (1.4 g, 7.9 mM).

$^1$H NMR (CDCl$_3$): δ 7.31-7.37 (m, 5H), 4.36-4.37 (m, 1H), 3.68 (s, 1H), 2.73-2.92 (m, 1H), 2.72 (d, J=10 Hz, 1H), 2.56-2.61 (m, 1H), 2.20-2.37 (m, 2H), 1.77-1.81 (m, 1H).

Step 3: Preparation of (3R)-1-benzyl-3-[(methylsulfonyl) oxy]pyrrolidine

The compound (3R)-1-benzyl-pyrrolidin-3-ol (1.0 g, 5.65 mM) was dissolved in triethylamine (2.0 ml, 14.3 mM), and dimethyl amino pyridine (DMAP) (0.002 g), dichloromethane (20.0 ml) and methanesulfonyl chloride (0.9 ml, 11.7 mM) was added dropwise at 0-5° C. The reaction mixture was maintained at the same temperature for about half an hour. The reaction mixture was then stirred at room temperature for 2 hours. The reaction mixture was diluted with dichloromethane (50.0 ml), washed with saturated sodium bicarbonate and brine solution. It was further dried over anhydrous sodium sulphate and concentrated to get the title compound as oil. Yield=95% (1.2 g, 5.38 mM). This material was used as such in the next step.

Step 4: Preparation of (3S)-1-benzyl-3-azidopyrrolidine

The compound (3R)-1-benzyl-3-[(methylsulfonyl) oxy] pyrrolidine (1.3 g, 5.8 mM) was dissolved in dimethylformamide (25.0 ml) and sodium azide (1.5 g, 23.3 mM) was added to it. The reaction mixture was maintained at 90-100° C. for about 12 hours followed by cooling at room temperature. The reaction mixture was poured into cold water (150.0 ml) with constant stirring. The organic compound was extracted with ethyl acetate and washed with water and brine solution, dried over anhydrous sodium sulphate and concentrated to give the title compound. Yield=78% (0.9 g, 4.5 m. This material was used as such in the next step.

IR (DCM): 2100.8 cm$^{-1}$.

Step 5: Preparation of (3S)-1-benzyl-3-aminopyrrolidine

The compound (3S)-1-benzyl-3-azidopyrrolidine (0.9 g, 4.5 mM) was dissolved in a mixture of tetrahydrofuran (36.0 ml) and water (7.0 ml). To it, triphenylphosphine (2.3 g, 8.9 mM) was added and the reaction mixture was refluxed for 7 hours. The reaction mixture was cooled to room temperature and tetrahydrofuran was evaporated under vacuum. The residue was taken in water (50.0 ml) and the pH was adjusted to about 2 and washed with chloroform. The pH of the aqueous solution was adjusted to about 12-13 with 1N sodium hydroxide and extracted with chloroform. The chloroform layer was washed with water and brine solution. It was further dried over anhydrous sodium sulphate and concentrated to give the title compound. Yield=62% (0.5 g, 2.8 mM).

$^1$HNMR (CDCl$_3$): δ 7.21-7.32 (m, 5H), 3.60 (d, J=4.3 Hz, 2H), 3.49-3.51 (m, 1H), 2.68-2.74m, 2H), 2.46-2.48 (m, 1H), 2.18-2.33 (m, 2H), 1.61 (s, 2H, —NH$_2$), 1.48-1.50 (m, 1H).

Step 6: Preparation of 2-cyclopentyl-2-hydroxy-N-[(3S)-1-benzyl-pyrrolidin-3-yl]-2-phenylacetamide (Compound No. 1)

The compound 2-cyclopentyl-2-hydroxy-2-phenylacetic acid (0.52 g, 2.36 mM) and (3S)-1-benzyl-3-aminopyrrolidine (0.5 g, 2.84 mM) were dissolved in dimethylformamide (10.0 ml) and N-methylmorpholine (1.3 ml, 11.8 mM) was added into it followed by the addition of 1-hydroxybenzotriazole (0.32 g, 2.36 mM) at 0-5° C. The reaction mixture was maintained at 0-5° C. for 1 hour and then at room temperature for 19 hours. The reaction mixture was poured into water (100.0 ml) with constant stirring. The organic compound was extracted with ethyl acetate. The ethyl acetate layer was washed with saturated sodium bicarbonate water and brine solution followed its drying and concentration over anhydrous sodium sulphate. The residue was purified by silica gel column chromatography using 10% methanol in chloroform to get the title compound. Yield=95% (0.5 g, 2.38 mM).

$^1$H NMR (CDCl$_3$): δ 7.58-7.60 (m, 2H), 7.26-7.36 (m, 8H), 6.74-6.80 (m, —CONH), 4.32-4.35 (m, 1H), 3.54-3.62 (m, 2H), 2.79-3.00 (m, 3H), 2.47-2.49 (brs, 1H, OH), 2.09-2.28 (m, 2H), 1.54-1.62 (m, 9H).

EXAMPLE 2

Preparation of 2-cyclopentyl-2-hydroxy-N-[(3S)-1-[2-(1,3-benzodioxol-5-yl)ethyl]pyrrolidin-3-yl]-2-phenylacetamide (Compound No. 2)

Step 1: Preparation of 2-cyclopentyl-2-hydroxy-N-[(3S)-pyrrolidin-3-yl]-2-phenylacetamide The compound 2-cyclopentyl-2-hydroxy-N-[(3S)-1-benzyl-pyrrolidin-3-yl]-2-phenyl-acetamide (0.8 g, 2.12 mM) was dissolved in methanol (20.0 ml) and 10% palladium on carbon (0.2 g) is added. After hydrogenating at room temperature for 10 hours at 65-70 psi, the second lot of 10% palladium on carbon (0.2 g) was added and hydrogenation was continued for 10 more hours at 65-70 psi at room temperature. The reaction mixture was diluted with methanol and filtered through a bed of hyflo. The filtrate was concentrated under vacuum and used as such in the next step.

Step 2: Preparation of 2-cyclopentyl-2-hydroxy-N-[(3S)-1-[2-(1,3-benzodioxol-5-yl)ethyl]pyrrolidin-3-yl]-2-phenylacetamide (Compound No. 2)

The compound 2-cyclopentyl-2-hydroxy-N-[(3S)-pyrrolidin-3-yl)]-2-phenylacetamide (0.3 g, 1.04 mM) was dissolved in acetonitrile (5.0 ml). To this, 5-(2-bromoethyl)-1,3-benzodioxole (0.28 g, 1.25 mM), potassium carbonate (0.43 g, 3.12 mM) and potassium iodide (0.34 g, 2.8 mM) were added and the reaction mixture was heated under reflux for 9 hours. The reaction mixture was cooled to room temperature and acetonitrile was evaporated under vacuum. The residue was partitioned between ethyl acetate (50.0 ml) and water (50.0 ml). The ethyl acetate layer was washed with water and brine solution and dried over anhydrous sodium sulphate and concentrated. The residue was purified by silica gel colum chromatography using 20% methanol in chloroform to get the title organic compound as an oil. Yield=64% (0.29 g, 0.67 mM).

$^1$H NMR (CDCl$_3$): δ 7.60 (d, J=7.5 Hz), 7.28-7.36 (m, 3H), 6.88 (br s, 1H, —CONH), 6.58-6.75 (m, 3H), 5.92 (d, J=1 Hz, 2H), 4.36-4.38 (m, 1H), 3.35-3.65 (brm, 1H), 2.88-3.03 (brm, 2H), 2.60-2.66 (m, 4H), 2.53 (m, 1H), 2.23-2.25 (m, 2H), 1.80 (brs, 1H, —OH), 1.55-1.66 (m, 9H).

EXAMPLE 3

Preparation of (3S)-1-benzyl-pyrrolidin-3-yl cyclopentyl (hydroxy) phenylacetate (Compound No. 3)

The compound 2-cyclopentyl-2-hydroxy-2-phenylacetic acid (0.3 g, 1.36 mM), (3R)-1-benzyl-pyrrolidin-3-ol (0.2 g, 1.14 mM) and triphenylphosphine (0.36 g, 1.36 mM) were dissolved in dry tetrahydrofuran (10.0 ml). To this, a solution of diethylazabicyclocarboxylate (0.2 ml, 1.36 mM) in dry tetrahydrofuran (2.0 ml) was added dropwise under nitrogen atmosphere at room temperature with constant stirring and the stirring was continued for 20 hours. Tetrahydrofuran was evaporated under vacuum and the residue was taken in chloroform and washed with saturated sodium bicarbonate solution, water and brine solution followed by drying and concentrating over anhydrous sodium sulphate. The residue was purified by silica gel column chromatography using 30% ethyl acetate in hexane to get the title compound as oil. Yield=91% (0.39 g, 1.03 mM).

$^1$H NMR (CDCl$_3$): δ 7.64-7.67 (m, 2H), 7.26-7.35 (m, 8H), 5.17-5.23 (m, 1H), 3.56-3.74 (m, 3H), 2.75-2.90 (m, 4H), 2.00-2.52 (m, 3H, including-OH), 1.29-2.00 (m, 8H).

EXAMPLE 4

Preparation of (3S)-1-[[2-(1,3-benzodioxol-5-yl)ethyl]pyrrolidin-3-yl]cyclopentyl(hydroxy)-phenylacetate (Compound No. 4)

Step 1: Preparation of (3S)-pyrrolidin-3-yl cyclopentyl (hydroxy) phenylacetate The compound (3S)-1-benzylpyrrolidin-3-yl cyclopentyl (hydroxy) phenylacetate (2.8 g, 7.4 mM) was dissolved in methanol (50.0 ml) and 10% palladium on carbon was added (0.28 g) followed by the addition of ammonium formate (1.5 g, 23.8 mM) under nitrogen atmosphere. The reaction mixture was maintained at 40-50° C. for 2 hours. One more lot of ammonium formate (1.5 g, 23.8 mM) was added and the reaction mixture was maintained at the same temperature for one more hour. The reaction mixture was cooled to room temperature and filtered through a bed of hyflo. The filtrate was evaporated under vacuum and the residue was taken in ethyl acetate and washed with water and brine solution and dried over anhydrous sodium sulphate and concentrated. It was used as such in the next step.

Step 2: Preparation of (3S)-1-[[2-(1,3-benzodioxol-5-yl)ethyl]pyrrolidin-3-yl]cyclopentyl(hydroxy)-phenylacetate (Compound No. 4)

The compound (3S)-pyrrolidine-3-yl cyclopentyl (hydroxy) phenylacetate (0.19 g, 0.66 mM) was dissolved in acetonitrile (5.0 ml) and 5-(2-bromoethyl)-1,3-benzodioxole (0.18 g, 0.79 mM) was added. To the reaction mixture, potassium carbonate (0.28 g, 1.97 mM) and potassium iodide (0.22 g, 1.31 mM) were added. The reaction mixture was heated under reflux for 9 hours. The reaction mixture was cooled to room temperature and acetonitrile was evaporated under vacuum. The residue was partitioned between ethyl acetate (30.0 ml) and water (30.0 ml). The organic layer was washed with water and brine solution followed by drying over anhydrous sodium sulphate and then concentrated. The residue was purified by silica gel column chromatography using 20% methanol in chloroform to get the title compound as oil. Yield=52% (0.15 g, 0.34 mM).

$^1$H NMR (CDCl$_3$): δ 7.65 (d, J=7.4 Hz, 2H), 7.30-7.35 (m, 3H), 6.61-6.74 (m, 3H), 5.92 (s, 2H), 5.21-5.23 (m, 1H), 3.78 (s, 1H), 2.54-2.92 (m, 7H), 2.05-2.45 (m, 2H), 1.83 (brss, —OH), 1.25-1.64 (m, 9H).

EXAMPLE 5

Preparation of (3S)-1-[[2-(2,3-dihydro-1-benzofuran-5-yl)ethyl]pyrrolidin-3-yl]cyclopentyl(hydroxy) phenylacetate (Compound No. 5)

The compound (3S)-pyrrolidin-3-yl cyclopentyl (hydroxy) phenylacetate (0.2 g, 0.69 mM) was dissolved in acetonitrile (5.0 ml) followed by the addition of 5-(2-bromoethyl)-2,3-dihydro-1-benzofuran (0.173 g, 0.76 mM), potassium carbonate (0.29 g, 2.01 mM) and potassium iodide (0.23 g, 1.38 mM). The reaction mixture was heated under reflux for 8 hours and then cooled to room temperature. Acetonitrile was evaporated under vacuum. The residue was partitioned between ethyl acetate (30.0 ml) and water (30.0 ml). The organic layer was washed with water and brine solution followed by drying over anhydrous sodium sulphate. The residue was purified by silica get column chromatography using 10% methanol in chloroform to get the title compound as oil. Yield=50% (0.15 g, 0.34 mM).

$^1$H NMR (CDCl$_3$): δ 7.66 (d, J=7 Hz, 2H), 7.31-7.36 (m, 3H), 7.03 (d, J=8 Hz, 1H), 6.93 (t, J=8 Hz, 1H), 6.69-672 (m, 1H), 5.22-5.24 (m, 1H), 4.55 (t, J=9 Hz, 2H), 3.76 (br m, 1H), 3.18 (t, J=9 Hz, 2H), 2.54-2.92 (m, 8H), 2.00-2.50 (m, 1H), 1.25-1.63 (m, 10OH, including —OH).

EXAMPLE 6

Preparation of (3S)-1-[(4-methyl-pent-3-enyl) pyrrolidin-3-yl]cyclopentyl (hydroxy)-phenylacetate (Compound No. 6)

The compound (3S)-pyrrolidin-3-yl cyclopentyl (hydroxy) phenylacetate (0.2 g, 0.69 mM) was dissolved in acetonitrile (5.0 ml) and 4-methyl-pent-3-enyl bromide (0.13 ml, 0.76 mM), potassium carbonate (0.29 g, 2.01 mM) and potassium iodide (0.23 g, 1.38 mM) were added into it. The reaction mixture was heated under reflux for 8 hours followed by cooling to room temperature. Acetonitrile was evaporated under vacuum. The residue was partitioned between ethyl acetate (30.0 ml) and water (30.0 ml). The organic layer was washed with water and brine solution. It was then dried over anhydrous Na$_2$SO$_4$ and concentrated. The residue was purified by silica gel column chromatography using 10% methanol in chloroform to get the title compound. Yield=54% (0.14 g, 0.38 mM) yield.

$^1$H NMR (CDCl$_3$): δ 7.55-7.66 (m, 2H), 7.30-7.34 (m, 3H), 5.60 (m, 1H), 5.06-5.24 (m, 1H), 4.32-4.71 (m, 2H), 3.58-3.75 (m, 3H), 2.83-3.25 (m, 3H), 2.22-2.33 (m, 3H, including —OH), 1.26-1.79 (m, 15H).

EXAMPLE 7

Preparation of (3S)-1-[[4-trifluoromethylphenyl)sulfonyl]pyrrolidin-3-yl]cyclopentyl(hydroxy) phenylacetate (Compound No. 7)

The compound (3S)-pyrrolidin-3-yl cyclopentyl (hydroxy) phenyl acetate (0.2 g, 0.69 mM) was dissolved in chloroform (10.0 ml) and triethylamine (0.19 ml, 1.38 mM) and dimethylaminopyridine (0.001 g) were subsequently added. The reaction mixture was cooled at 0-5° C. 4-(trifluoromethyl) benzenesulfonyl chloride (0.2 g, 083 mM) was added to it and maintained for 2 hours at the same temperature and then at room temperature for overnight. The reaction mixture was diluted and the organic layer was washed with water and brine solution. It was finally dried over anhydrous sodium sulphate and concentrated. The residue was purified by silica gel column chromatography using 40% ethyl acetate in hexane to get the title compound. Yield=70% (0.24 g, 0.48 mM).

$^1$H NMR (CDCl$_3$): δ 7.97-7.99 (m, 2H), 7.83-7.87 (m, 2H), 7.27-7.42 (m, 5H), 5.22-5.28 (brm, 1H), 3.32-3.57 (m, 6H), 2.50-2.75 (m, 1H), 2.08-2.10 (brss, 1H), 1.26-1.82 (m, 8H).

EXAMPLE 8

Preparation of (3S)-1-[[4-nitrophenyl) sulfonyl]pyrrolidin-3-yl]cyclopentyl (hydroxy)phenyl acetate (Compound No. 8)

The compound (3S)-pyrrolidin-3-yl cyclopentyl (hydroxy) phenylacetate (0.2 g, 0.69 mM) was dissolved in chloroform (10.0 ml). To the reaction mixture triethylamine (0.19 ml, 1.38 mM) and dimethylaminopyridine (0.001 g) were added and cooled the resulting reaction mixture to 0-5° C. 4-(nitro) benzenesulfonyl chloride (0.184 g, 083 mM) was added to it and maintained for 2 hour and the reaction was quenched by adding saturated sodium bicarbonate solution (5.0 ml). The organic layer was washed with water and brine solution, which was dried over anhydrous sodium sulphate and concentrated. The residue was purified by silica gel column chromatography using 40% ethyl acetate in hexane to get the title compound. Yield=76% (0.25 g, 0.53 mM).

$^1$H NMR (CDCl$_3$): δ 8.37-8.43 (m, 2H), 7.99-8.07 (m, 2H), 7.29-7.44 (m, 5H), 5.23-5.27 (m, 1H), 3.28-3.60 (m, 6H), 2.50-2.75 (m, 1H), 2.10-2.13 (brs, 1H), 1.23-1.60 (m, 8H).

EXAMPLE 9

Preparation of (3S)-1-benzylpyrrolidin-3-yl (2R)-hydroxy (3-oxocyclopentyl) phenyl acetate (Compound No. 9)

The compounds (2R)-hydroxy (3-oxocyclopentyl) phenylacetic acid (1.0 g, 4.27 mM), (3R)-1-benzyl-pyrrolidin-3-ol (0.63 g, 3.56 mM) were dissolved in dry tetrahydrofuran (30 ml) and triphenylphosphine (1.12 g, 4.27 mM). To the reaction mixture, a solution of diethylazoldicarboxyate (0.7 ml, 4.27 mM) in dry tetrahydrofuran (4.0 ml) was added dropwise under nitrogen atmosphere at room temperature with constant stirring and stirring was continued for 20 hours at the same temperature. Tetrahydrofuran was evaporated under vacuum and the residue was purified by silica gel column chromatography using 35% ethyl acetate in hexane to get the title compound. Yield=11% (0.18 g, 0.46 mM).

$^1$H NMR (CDCl$_3$): δ 7.61-7.67 (m, 2H), 7.30-7.40 (m, 8H), 5.18-5.23 (m, 1H), 3.88 (brs, —OH), 3.57-3.70 (m, 2H), 3.21 (m, 1H), 2.68-2.80 (m, 3H), 2.39-2.44 (m, 1H), 2.12-2.27 (m, 4H), 1.61-1.81 (m, 4H).

EXAMPLE 10

Preparation of (3S)-1-benzylpyrrolidin-3-yl (2R)-hydroxy (3-hydroxycyclopentyl) phenyl acetate (Compound No. 10)

The compound (3S)-1-benzylpyrrolidin-3-yl (2R)-hydroxy (3-oxocyclopentyl) phenylacetate (0.5 g, 1.27 mM) was dissolved in methanol (25.0 ml). To the reaction mixture, sodium borohydride (0.24 g, 6.36 mM) was added in several portions at −78° C. and maintained the resulting reaction mixture at the same temperature for 1 hour. The reaction mixture was diluted with water (10.0 ml) and brought to room temperature. Methanol was removed under vacuum and the organic layer was extracted with chloroform. The organic layer was washed with water and brine solution and dried over anhydrous sodium sulphate and concentrated. The residue was purified by silica gel column chromatography using 60% ethyl acetate in hexane to get the title compound. Yield=46% (0.23 g, 0.58 mM).

$^1$H NMR (CDCl$_3$): δ 7.63 7.66 (m, 2H), 7.28-7.37 (m, 8H), 5.19-5.22 (m, 1H), 4.35 (br s, secondary —OH), 4.11-4.19 (m, 1H), 3.55-3.72 (m, 2H), 3.25 (m, 1H), 2.66-2.82 (m, 3H), 2.45 (m, 1H), 2.17-2.20 (m, 1H), 1.95 (m, 1H), 1.42-1.82 (m, 7H, including quaternary —OH).

EXAMPLE 11

Preparation of (3S)-1-[(phenyl acetyl)]pyrrolidin-3-yl cyclopentyl(hydroxy)phenyl acetate (Compound NO. 11)

The compound (3S)-pyrrolidin-3-yl cyclopentyl (hydroxy) phenyl acetate (0.2 g, 0.69 mM) was dissolved in chloroform (10.0 ml). To the reaction mixture, triethylamine (0.19 ml, 1.38 mM) and dimethyl amino pyridine (DMAP) (0.001 g) were added and cooled to 0-5° C. Phenyl acetyl chloride (0.12 ml, 0.83 mM) was added to it and maintained the resulting mixture at the same temperature for 2 hours and then at room temperature overnight. The reaction mixture was diluted with chloroform and the reaction was quenched by adding saturated sodium bicarbonate solution (5.0 ml). The organic layer was washed with water and brine solution which was finally dried over anhydrous sodium sulphate and concentrated. The residue was purified by silica gel column chromatography using 40% ethyl acetate in hexane to get the title compound. Yield=53% (0.15 g, 0.37 mM).

$^1$H NMR (CDCl$_3$): δ 7.46-7.55 (m, 2H), 7.19-7.34 (m, 8H), 5.32-5.33 (m, 1H), 3.59-3.71 (m, 4H), 3.46-3.54 (m, 2H) 2.15-2.17 (m, 1H) 1.54-1.59 (m, 2H), 1.45-1.50 (m, 7H), 1.25-1.37 (m, 2H).

EXAMPLE 12

Preparation of (3S)-1-[(benzyloxyacetyl)]pyrrolidin-3-yl cyclopentyl (hydroxy)phenyl acetate (Compound No. 12)

The compound (3S)-pyrrolidin-3-yl cyclopentyl (hydroxy) phenylacetate (0.2 g, 0.69 mM) was dissolved in chloroform (10.0 ml). To the reaction mixture, triethylamine (0.19 ml, 1.38 mM) and dimethyl amino pyridine (DMAP) (0.001 g) were added and cooled to 0-5° C. Benzyloxyacetyl chloride (0.14 ml, 083 mM) was added to it and the reaction mixture was maintained at the same temperature for two hours, then at room temperature overnight. The reaction mixture was diluted with chloroform and the reaction was quenched by adding saturated sodium bicarbonate solution (5.0 ml). The organic layer was washed with water and brine solution, dried over anhydrous sodium sulphate and concentrated. The residue was purified by silica gel column chromatography using 40% ethyl acetate in hexane to get the title compound. Yield=66% (0.2 g, 0.46 mM).

$^1$H NMR (CDCl$_3$): δ 7.53-7.59 (m, 2H), 7.25-7.38 (m, 8H), 5.34 (brm, 1H), 4.52-4.67 (m, 2H), 4.09-4.26 (m, 1H), 3.62-3.84 (m, 4H), 3.49-3.52 (m, 1H), 2.85 (brm, 1H), 1.92-2.20 (m, 2H), 47-1.54 (m, 7H), 1.26-1.34 (m, 2H).

EXAMPLE 13

Preparation of Benzyl (3S)-3-[2-hydroxy-2-cyclopentyl-2-phenylpropanoyl) oxy]pyrrolidine-1-carboxyate (Compound No. 13)

The compound (3S)-pyrrolidin-3-yl cyclopentyl (hydroxy) phenylacetate (0.2 g, 0.69 mM) was dissolved in chloroform (10.0 ml). To the reaction mixture, triethylamine (0.19 ml, 1.38 mM) and dimethyl amino pyridine (DMAP) (0.001) were added and cooled to 0-5° C. Benzylchloroformate (0.24 ml, 083 mM) was added to it and maintained the reaction mixture at the same temperature for two hours and then at room temperature overnight. The reaction mixture was diluted with chloroform and the reaction was quenched by adding saturated sodium bicarbonate solution (5.0 ml). The organic layer was washed with water and brine solution, dried over anhydrous sodium sulphate and concentrated. The residue was purified by silica gel column chromatography using 40% ethyl acetate in hexane to get the title compound. Yield=65% (0.19 g, 0.45 mM).

$^1$H NMR (CDCl$_3$): δ 7.57-7.61 (m, 2H), 7.30=7.38 (m, 8H), 5.32 (brm, 1H), 5.10-5.17 (m, 2H), 3.38-3.68 (m, 5H), 2.85-2.90 (brm, 1H), 2.13 (brs, 1H), 1.88-1.90 (m, 1H), 1.21-1.47 (m, 8H).

EXAMPLE 14

Preparation of (3S)-1-[(4-bromophenyl)]pyrrolidin-3-yl] cyclopentyl (hydroxy)phenyl acetate (Compound No. 14)

The compound (3S)-pyrrodidin-3-yl cyclopentyl(hydroxy)phenyl acetate (0.2 g, 0.69 mM) was dissolved in chloroform (10.0 ml). To the reaction mixture, triethylamine (0.19 ml, 1.38 mM) and dimethyl amino pyridine DMAP (0.001 g) were added and cooled to 0-5° C. 4-bromo benzenesulfonyl chloride (0.21 g, 083 mM) was added to it and the reaction mixture was maintained at the same temperature for two hours and then at room temperature overnight. The reaction mixture was diluted with chloroform and the reaction was quenched by adding saturated sodium bicarbonate solution (5.0 ml). The organic layer was washed with water and brine solution, dried over anhydrous sodium sulphate and concentrated. The residue was purified by silica gel column chromatography using 40% ethyl acetate in hexane to get the title compound as a gummy solid. Yield=43% (0.15 g, 0.3 mM).

$^1$H NMR (CDCl$_3$): δ 7.73-7.74 (m, 4H), 7.28-7.41 (m, 5H), 5.18-5.28 (brd, 1H), 3.25-3.56 (m, 5H), 2.50-2.75 (m, 1H), 2.08-2.10 (brs, 1H), 1.26-1.65 (m, 9H).

EXAMPLE 15

Preparation of (3S)-1-benzyl-pyrrolidin-3-yl (2R)-cyclopentyl (hydroxy) phenyl acetate (Compound No. 15)

The compounds (2R)-hydroxy (3-oxocyclopentyl)-2-hydroxy-2-phenylacetic acid (3.0 g, 13.6 mM), (3R)-1-benzyl-pyrrolidin-3-ol (2.0 g, 11.4 mM) were dissolved in dry tetrahydrofuran (80.0 ml) and triphenylphosphine (3.6 mM). To the reaction mixture, a solution of diisopropyl azadicarboxylate (2.7 ml, 13.6 mM) in dry tetrahydrofuran (20.0 ml) was added dropwise under nitrogen atmosphere at room temperature with constant stirring and the stirring was continued for 20 hours at room temperature. Tetrahydrofuran was evaporated under vacuum and the residue was taken in chloroform and washed with saturated sodium bicarbonate solution, water and brine solution, dried over anhydrous sodium sulphate and concentrated. The residue was purified by silica gel column chromatography using 15% ethyl acetate in hexane to get the title compound. Yield=23% (1.2 g, 3.17 mM).

$^1$H NMR (CDCl$_3$): δ 7.65-7.67 (m, 2H), 7.26-7.36 (m, 8H), 5.16-5.21 (m, 1H), 3.56-3.75 (m, 3H), 2.70-2.81 (m, 4H), 2.50-2.60 (m, 1H), 2.10-2.30 (m, 1H), 1.26-1.90 (m, 9H).

EXAMPLE 16

Preparation of (3S)-1-[[2-(2,3-dihydro-1-benzofuran-5-yl)ethyl]pyrrolidin-3-yl] (2R)-cyclopentyl(hydroxy)phenyl acetate (Compound No. 16)

The compound (3S)-pyrrolidin-3-yl (2R)-cyclopentyl (hydroxy) phenyl acetate (0.2 g, 0.69 mM) was dissolved in acetonitrile (5.0 ml). To the reaction mixture, 5-(2-bromoethyl)-2,3-dihydro-1-benzofuran (0.173 g, 0.76 mM), potassium carbonate (0.29 g, 2.01 mM) and potassium iodide (0.23 g, 1.38 mM) were added and the reaction mixture was heated under reflux for 8 hours and then cooled to room temperature. Acetonitrile was evaporated under vacuum. The residue was partitioned between ethyl acetate (30.0 ml) and water (30.0 ml). The organic layer was washed with water and brine solution. It was dried over anhydrous Na$_2$SO$_4$ and concentrated. The residue was purified by silica gel column chromatography using 30% ethyl acetate in hexane to get the title compound. Yield=46% (0.14 g, 0.32 mM).

$^1$H NMR (CDCl$_3$): δ 7.66 (D, J=1.5 Hz, 2H), 7.28-7.36 (m, 3H), 7.05 (d, J=8 Hz, 1H), 6.94 (d, J=8 Hz, 1H), 6.71 (d, J=8 Hz, 1H), 5.20-5.23 (m, 1H), 4.52-4.58 (m, 2H), 3.80 (s, 1H), 3.18 (t, J=9 Hz, 2H), 2.70-2.92 (m, 8H), 2.50-2.70 (m, 1H), 2.04-2.15 (m, 1H), 1.25-1.61 (m, 9H).

EXAMPLE 17

Preparation of (3S)-1-[[2-(1,3-benzodioxol-5-yl) ethyl]pyrrolidin-3-yl] (2R)-cyclopentyl(hydroxy) phenyl acetate (Compound No. 17)

The compound (3S)-pyrrolidin-3-yl (2R)-cyclopentyl (hydroxy) phenylacetate (0.19 g, 0.66 mM) was dissolved in acetonitrile (5.0 ml). To the reaction mixture, 5-(2-bromoethyl)-1,3-benzodioxole (0.18 g, 0.79 mM), potassium carbonate (0.28 g, 1.97 mM) and potassium iodide (0.22 g, 1.31 mM) were added and the reaction mixture was heated under reflux for 9 hours and then cooled to room temperature. Acetonitrile was evaporated under vacuum. The residue was partitioned between ethyl acetate (30.0 ml) and water (30.0 ml). The organic layer was washed with water and brine solution, dried over anhydrous sodium sulphate and concentrated. The residue was purified by silica gel column chromatography using 30% ethyl acetate in hexane to get the title compound. Yield=43% (0.12 g, 0.27 mM).

$^1$H NMR (CDCl$_3$): δ 7.65 (d, J=7.5 Hz, 2H), 7.28-7.36 (m, 3H), 6.64-6.75 (m, 3H), 5.92 (s, 2H), 5.19-5.24 (m, 1H), 3.79 (s, 1H), 2.63-2.92 (m, 7H), 2.45-2.65 (m, 1H), 2.05-2.30 (m, 1H), 1.23-1.80 (m, 10H).

Biological Activity

Radioligand Binding Assays:

The affinity of test compounds for $M_2$ and $M_3$ muscarinic receptor subtypes was determined by [$^3$H]-N-methyl scopolamine binding studies using rat heart and submandibular gland, respectively as described by Moriya et al., (*Life Sci.* 1999,64(25): 2351-2358) with minor modifications.

Membrane preparation: Submandibular glands and heart were isolated and placed in ice cold homogenizing buffer (HEPES 20 mM, 10 mM EDTA, pH 7.4) immediately after sacrifice. The tissues were homogenized in 10 volumes of homogenizing buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −70° C. until the time of assay.

Ligand binding assay: The compounds were dissolved and diluted in DMSO. The membrane homogenates (150-250 µg protein) were incubated in 250 µl of assay buffer (HEPES 20 mM, pH 7.4) at 24-25° C. for 3 hours. Non-specific binding was determined in the presence of 1 µM atropine. The incubation was terminated by vacuum filtration over GF/B fiber filters (Wallac). The filters were then washed with ice-cold 50 mM Tris HCl buffer (pH 7.4). The filter mats were dried and bound radioactivity retained on filters was counted. The $IC_{50}$ & Kd were estimated by using the non-linear curve-fitting program using G Pad Prism software. The value of inhibition constant Ki was calculated from competitive binding studies by using Cheng & Prusoff equation (*Biochem Pharmacol,* 1973.22: 3099-3108), $Ki=IC_{50}/(1+L/Kd)$, where L is the concentration of [$^3$]NMS used in the particular experiment.

Functional Experiments Using Isolated Rat Bladder:

Methodology:

Animal were euthanized by overdose of urethane and whole bladder was isolated and removed rapidly and placed in ice cold Tyrode buffer with the following composition (mMol/L) sodium chloride 137; KCl 2.7, $CaCl_2$ 1.8, $MgCl_2$ 0.1; $NaHCO_3$ 11.9, $NaH_2PO_4$ 0.4; Glucose 5.55 and continuously gassed with 95% $O_2$ and 5% $CO_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period, the stabilization of the tissue contractile response was assessed with 1 µmol/L of carbachol consecutively for 2-3 times. Subsequently, a cumulative concentration response curve to carbachol ($10^{-9}$ mol/L to $3\times10^{-5}$ mol/L) was obtained. After several washes, once the baseline was achieved, cumulative concentration response curve was obtained in the presence of NCE (NCE added 20 min. prior to the second CRC).

The contractile results were expressed as % of control E max ED50 values were calculated by fitting a non-linear regression curve (Graph Pad Prism). pKB values were calculated by the formula pKB=−log [(molar concentration of antagonist/(dose ratio-1))]

where, dose ratio=ED50 in the presence of antagonist/ED50 in the absence of antagonist.

The results of the in-vitro tests are listed in Table II.

In-Vitro Test

TABLE II

| | Receptor Binding Assay | | Functional Assay |
|---|---|---|---|
| | $M_2$ PKi | $M_3$ pki | $pK_B$ |
| Compound No. 1 | <5 | <5 | — |
| Compound No. 2 | 5.75 | 6.97 | — |

TABLE II-continued

| | Receptor Binding Assay | | Functional Assay |
|---|---|---|---|
| | $M_2$ PKi | $M_3$ pki | $pK_B$ |
| Compound No. 3 | 6.13 | 7.17 | 7.54 |
| Compound No. 4 | 7.32 | 8.39 | 7.36 |
| Compound No. 5 | 6.93 | 8.02 | 8.69 |
| Compound No. 6 | 6.74 | 7.87 | 7.84 |
| Compound No. 7 | 6.82 | 7.39 | — |
| Compound No. 8 | 6.58 | 7.25 | — |
| Compound No. 9 | <5 | 6.9 | — |
| Compound No. 10 | 5.33 | 6.81 | — |
| Compound No. 11 | <6 | <6 | — |
| Compound No. 12 | 6.74 | 7.34 | — |
| Compound No. 13 | 6.39 | 6.7 | — |
| Compound No. 14 | 6.77 | 7.4 | — |
| Compound No. 15 | 6.6 | 8.0 | — |
| Compound No. 16 | 6.9 | 8.0 | — |
| Compound No. 17 | 7.4 | 8.5 | — |
| Oxybutynin | 8.00 | 9.46 | 8.93 |
| Tolterodine | 8.16 | 8.15 | 8.89 |

While the present invention has been described in terms of its specific embodiments, certain modifications and equivalents will be apparent to those skilled in the art and are intended to be included within the scope of the present invention.

We claim:

1. A compound selected from the group consisting of:
   2-cyclopentyl-2-hydroxy-N-[(3S)-1-benzyl-pyrrolidin-3-yl]-2-phenyl acetamide;
   2-cyclopentyl-2-hydroxy-N-[(3S)-1-[2-(1,3-benzodioxol-5-yl)ethyl]pyrrolidin-3-yl]-2-phenyl acetamide;
   (3S)-1-[[2-(1,3-benzodioxol-yl)ethyl]pyrrolidin-3-yl]-2-cyclopentyl-2-(hydroxy)-2-phenyl acetate;
   (3S)-1-[[2(2,3-dihydro-1-benzofuran-5-yl)ethyl]pyrrolidin-3-yl]-2-cyclopentyl-2-(hydroxy)-2-phenyl acetate;
   (3S)-1-[(4-methyl-pent-3-enyl)pyrrolidin-3-yl]-2-cyclopentyl-2-(hydroxy)-2-phenyl acetate;
   (3S)-1-[(4-trifluoromethylphenyl)sulfonyl]pyrrolidin-3-yl]-2-cyclopentyl-2-(hydroxy)-2-phenyl acetate;
   (3S)-1-[(4-nitrophenyl)sulfonyl]pyrrolidin-3-yl]-2-cyclopentyl-2-(hydroxy)-2-phenyl acetate;
   (3S)-1-benzyl-pyrrolidin-3-yl (2R)-2-hydroxy-2-(3-oxo-cyclopentyl)-2-phenyl acetate;
   (3S)-1-benzyl-pyrrolidin-3-yl (2R)-hydroxy-2-(3-hydroxycyclopentyl)-2-phenyl acetate;
   (3S)-1-[(phenyl acetyl)pyrrolidin-3-yl]-2-cyclopentyl-2-(hydroxy)-2-phenyl acetate;
   (3S)-1-[(benzyloxy)acetyl)]pyrrolidin-3-yl]-2-cyclopentyl-2-(hydroxy)-2-phenyl acetate;
   Benzyl (3S)-3-[(2-hydroxy-2-cyclopentyl-2-phenylpropanoyl)oxy]pyrrolidin-1-carboxylate;
   (3S)-1-[(4-bromophenyl)sulfonyl]pyrrolidin-3-yl]-2-cyclopentyl-2-hydroxy)-2-phenyl acetate;
   (3S)-1-benzyl-pyrrolidin-3-yl (2R)-cyclopental-2-(hydroxy)-2-phenyl acetate;
   (3S)-1-[[2-(2,3-dihydro-1-benzofuran-5-yl)ethyl]pyrrolidin-3-yl](2R)-cyclopentyl-2-(hydroxy)-2-phenyl acetate; and,
   (3S)-1-[[2-(1,3-benzodioxol-5-yl)ethyl]pyrrolidin-3-yl] (2R)-cyclopentyl-2-(hydroxy)-2-phenyl acetate.

2. A pharmaceutical composition comprising a therapeutically effective amount of a compound as defined in claim 1 optionally together with pharmaceutically acceptable carriers, excipients or diluents.

* * * * *